United States Patent [19]

Rosenthal et al.

[11] Patent Number: 5,132,230
[45] Date of Patent: Jul. 21, 1992

[54] PRIMARY STANDARD AND METHOD OF MAKING SECONDARY STANDARDS FOR CALIBRATION OF GLYCATED PROTEIN ASSAYS

[75] Inventors: Murray A. Rosenthal; Michael E. Jackson, both of Akron, Ohio

[73] Assignee: Isolab, Inc., Akron, Ohio

[21] Appl. No.: 329,591

[22] Filed: Mar. 28, 1989

[51] Int. Cl.$^5$ .................. G01N 33/66; G01N 33/68
[52] U.S. Cl. ........................................ 436/15; 436/8; 436/14; 436/87; 436/88; 436/95; 436/904
[58] Field of Search ........................ 436/8–18, 436/34, 87, 88, 95, 164.63, 67, 904; 252/408.1; 422/61; 530/322, 345, 380, 389, 395, 402, 406, 410

[56] References Cited

U.S. PATENT DOCUMENTS

| | | | |
|---|---|---|---|
| 4,274,978 | 6/1981 | Moore | 436/14 |
| 4,629,692 | 12/1986 | Dean | 436/67 X |
| 4,642,295 | 2/1987 | Baker | 436/14 |
| 4,645,742 | 2/1987 | Baker | 436/14 |
| 4,665,192 | 5/1987 | Cerami | 435/7.94 X |
| 4,758,583 | 7/1988 | Cerami | 514/631 X |

OTHER PUBLICATIONS

Kennedy et al, Diebetes, vol. 29, pp. 413–415, 1980.
Day et al, J. Bio. Chem., vol. 254, No. 3, pp. 595–597; 1979.

*Primary Examiner*—Robert J. Hill, Jr.
*Attorney, Agent, or Firm*—Roger A. Gilcrest

[57] ABSTRACT

This invention provides a primary standard and/or secondary standards for assay for glycated proteins in samples such as blood. The primary standard is composed of a polymer or copolymer of an amino acid, such as lysine, serine or those listed on table 37 (pages 100–110 of the second edition of Organic Chemistry by Robert Morris and Robert Nielson-Boyd) glycated with a known amount of glucose, preferably $^{14}C$ glucose or $^3H$ glucose, and free of unbound glucose. The preferred secondary standards are composed of glycated native protein per se, or a mixture of a glycated native protein and native protein that has been standardized against a primary standard to give the actual glycated protein value. These primary standards and secondary standards may be packaged and sold as a kit that contains a primary standard and/or a secondary standard and the reagents needed to perform the glycated protein assay. These glycated proteins or glycated polyamino acids can be dyed to give colored products for use as standards for the so-called affinity or ion exchange column assays, used to measure glycated protein percentage.

7 Claims, 1 Drawing Sheet

PRIMARY STANDARD AND METHOD OF MAKING SECONDARY STANDARDS FOR CALIBRATION OF GLYCATED PROTEIN ASSAYS

TECHNICAL FIELD

This invention relates to methods of providing standards for use in the calibration and control of assays involving the measurement of glycated proteins and said standards. Glycated protein assays are used in detecting diabetes and/or deciding treatment levels for diabetic patients as well as determining glycated protein levels.

BACKGROUND ART

Up to now, there have been no primary standards available for use with glycated protein assays. Controls and calibrators do exist, but they are only assigned values by either:

1) assaying secondary standards alongside the control and extrapolating the value for that control or 2) initially and arbitrarily assigning a value to a control and attempting to match subsequent control values to this initial control value by running known and unknown controls side by side and extrapolating. Thus the lack of a primary standard is a source of error in these assays. An example of using a secondary standard to calibrate an assay is the fructosamine assay as taught by Baker in U.S. Pat. Nos. 4,642,295 and 4,645,742 or Rosenthal in EPO Patent Application 85/307,206. In these patents, 1-deoxy-1-morpholinofructose (DMF) is used in an aqueous solution of a protein to standardize the reaction. DMF is considered a secondary standard because it reacts in a similar fashion to glycated protein in the fructosamine assay. DMF cannot be considered a primary standard because it is not a glycated protein. An example of a control value being arbitrarily assigned in the hemoglobin $A_1$ (Hb $A_1$) assay is that of Acuff et al.'s U.S. Pat. No. 4,238,196. In this assay, columns which measure glycated hemoglobin (Hb $A_1$) are used to initially assign a value to a pooled hemoglobin control, and subsequent batches of both columns and controls are matched to the value of this initial control.

The major difficulty involved in preparing a primary protein standard is the unavailability of a starting material that is not glycated. The major sources of starting material for controls are human or animal blood products including serum, plasma, red cells (hemoglobin), and albumin. These protein sources are all glycated to some extent. One approach to obtaining nonglycated protein would be to separate the non-glycated protein from the glycated protein using chromatography. The principal disadvantages of this approach are:

(a) Proteins may be denatured to some extent during chromatography.

(b) Large amounts of protein are needed and this would require the use of large columns which are difficult and time-consuming to run.

(c) The resulting nonglycated product may still be glycated to some degree.

The non-availability of a primary standard for measuring glycated protein has made calibration of the various assays difficult indeed. This is probably best illustrated in the fructosamine assay. Phillipou et al., Clinical Chem. 34 1561 (1988), point out that DMF, on reaction with nitro blue tetrazolium chloride (NBT), gives a different visible spectrum clearly dissimilar from that obtained for protein or plasma samples. Addition of protein to the DMF solution before introduction of the NBT reagent changed DMF's spectral characteristics to mimic those observed for serum samples. The use of DMF/protein calibrators has several practical limitations and Phillipou et al. above, referenced 15 publications addressing the question of assay standardization and problems thereof. One particularly thorny problem is that the addition of protein to DMF solutions adds an unknown amount of fructosamine to each calibrator. Another problem is that there is no true zero standard because all available proteins are glycated. Phillipou et al. also point out that the use of DMF as a calibrant causes overestimation of the amount of fructosamine present in a plasma sample.

DISCLOSURE OF INVENTION

The first aspect of this invention is the quantitative glycosylation of a synthetic poly-amino acid such as poly-L-lysine. Synthetic polymers of amino acids are not natively glycated, i.e., they do not inherently contain some glucose reacted thereto as do native proteins. Our primary standard in our specific embodiment is made by incubation of poly-L-lysine with glucose and quantitation of the amount of glucose incorporated into the polymer. The glycated polymer is a primary standard and can then be mixed with known amounts of nonglycated polymer and used to standardize various glycated protein assays. Protein containing secondary standards, containing an unknown amount of glycation, can be assigned against values based on the primary standards to give more accurate results.

The second aspect of this invention is the quantitative glycation of a protein or a mixture of proteins, which originally contain an unknown amount of native glycation. The amount of native glycation is then determined by 1) mixing known proportions of glucose-incubated protein and non-glucose incubated protein, i.e., native protein then 2) obtaining a measurement of the glycation of each mixture by a glycated protein assay, and 3) extrapolating this measurement to zero glucose concentration of the glucose incubated protein.

Quantitation of the extent of glycosylation which occurs during in vitro incubation of glucose with poly-L-lysine, or other polymers of amino acids or blends of amino acids, can be accomplished by:

1) measuring the amount of glucose remaining in solution after incubation and subtracting from the amount of glucose originally present;

2) incubating with a labeled glucose, i.e. $^{14}C$ or $^3H$ glucose, and measuring the incorporated and/or unincorporated label glucose via liquid scintillation counting or other radioactivity monitoring technique; or 3) incubation with istopically labeled glucose such as $^{13}C$-glucose, and measuring the incorporated an/or unincorporated label glucose via standard isotopic measurement techniques (example: $^{13}C$ NMR).

The use of poly-L-lysine or other polyamino acids as an "artificial protein" with zero glycosylation is the basis for the first aspect of this invention. Any soluble homopolymer, copolymer, or random copolymer of any mixture of amino acids (such as those found on pages 100–110 of the Second Edition of "Organic Chemistry" by Robert Morris and Robert Nielson-Boyd) for use as a nonglycated starting material is possible. Since all polyamino acids have an amino-terminus, viz. N-terminus, available to react with glucose, they all theoretically could be used for this purpose. Incorporation of lysine in the polyamino acids would however increase the sites available for glycation by increasing the number of free amino groups. Examples of random copolymers which can be used are Poly (Lysine-Serine), Poly (Lysine-Alanine), Poly (Lysine-Glycine), Poly (Lysine-Alanine-Glutamic acid-Tyrosine). Examples of polyamino acid homopolymers which can be used are Poly-D-Lysine, Poly-D,L-Lysine. These polymers have a broad range of molecular weights of a few thousands to over a million. The preferred ones are water soluble and are about 10,000 to 150,000 molecular weight. The primary standard may contain a known reacted glucose content greater than 0 to 15 millimoles per liter of aqueous standard solution.

Incubation with glucose can be accomplished in aqueous solution, preferably under conditions which promote the formation of the Amadori rearrangement product of the Schiff base adduct formed between glucose and the amino groups of protein and the synthetic amino acid polymers. These conditions include glucose and protein concentration, time, temperature and pH. These conditions are several hours to days at about 2° to 100° C. at a pH of about 6.5 to 9.5. Care must be taken in order to assure minimal denaturation of the protein. Sterility is also important because microbes may metabolize glucose causing loss of analyate. It is also advantageous to remove unreacted glucose upon completion of the reaction, so that no further reaction occurs. Unreacted glucose can be removed by dialysis or gel filtration. Then the unreacted glucose removed as dialysate or filtrate is measured by known glucose assay methods, and used to calculate the degree of glycation of the polymer. Alternatively, if isotopically labeled glucose is used, the degree of glycation is measured using standard techniques.

There are numerous well known techniques and assays which may be used to measure glycated protein or glycated hemoglobin. These methods include the well known fructosamine assay, ion-exchange chromatography, and the so called affinity chromatography, phenylhydrazine derivatization, furosine procedure, thiobarbituric acid procedure, and the periodate procedure. All of these assays could use these primary standards and their primary standard derived secondary standards to give more precise assays of the glycated protein.

As an adjunct to this method, quantitatively glycated primary standards could be used to assign or define values for secondary standards, controls, and/or calibrators. This can be done by assaying the standard and an unknown side by side, and assigning the obtained value of the known to the unknown, which now becomes a secondary standard, control, or calibrator. Unknowns would include any protein solution such as synthetic glycated polylysine, poly-L-lysine, poly-D-lysine, or native proteins like serum, plasma, hemoglobin or albumin. These unknowns could be stored in one of several states including frozen, liquid, or lyophilized to await their use.

BRIEF DESCRIPTION OF THE DRAWINGS

The FIGURE shows a plot of the amount of glyco groups (x-axis) versus absorbance (y-axis) for a fructosamine standard in accordance with Example 2 below.

BEST MODE FOR CARRYING OUT THE INVENTION

Figure 1:
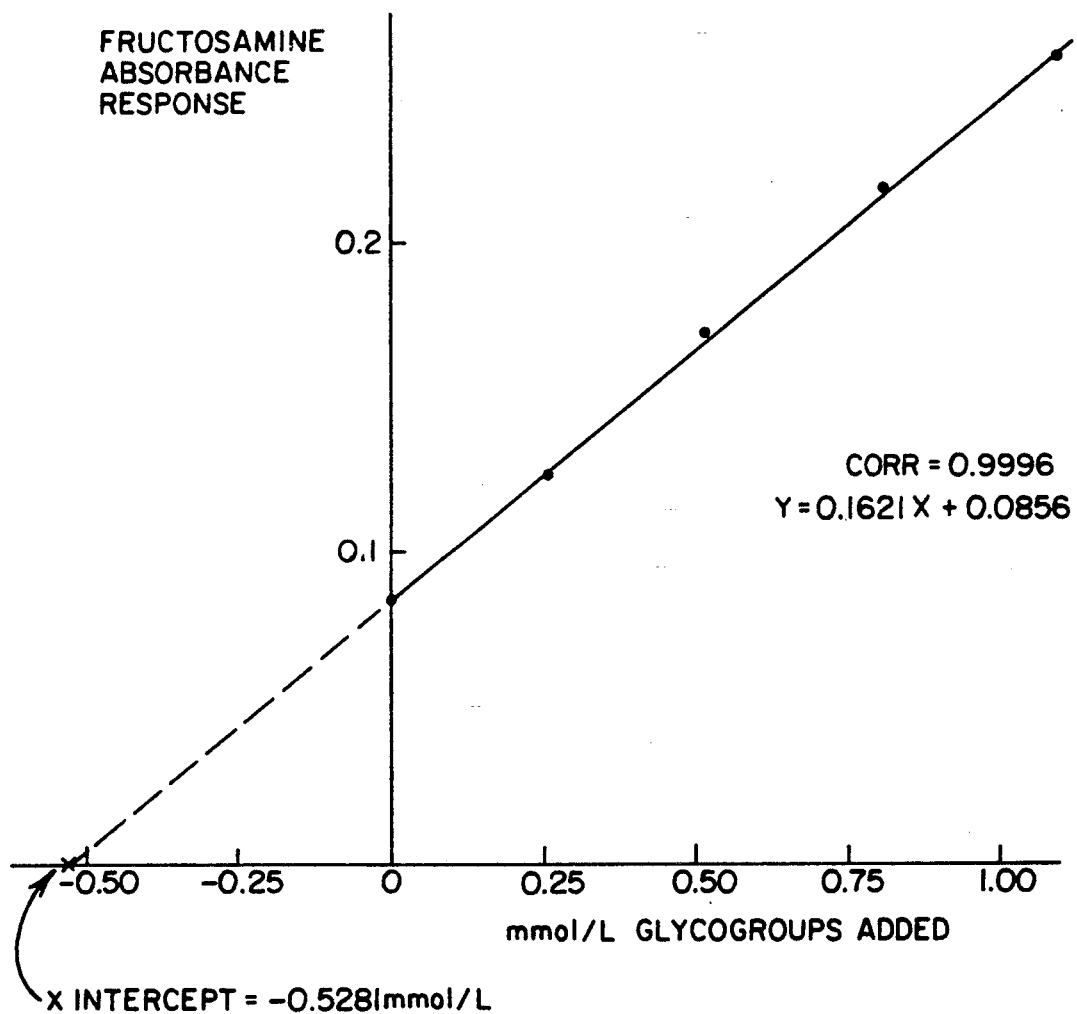

In one aspect of this invention, poly-L-lysine (or a related polymer of amino acids), is incubated with [$^{14}$C]glucose at pH 8.0 for two days at 60° C. The unbound glucose is removed by dialysis and the product may be lyophilized. An equivalent portion of poly-L-lysine or polymer of amino acids is treated in the above manner, except no glucose is included. The amount of glucose bound to the glucose-incubated product is determined by liquid scintillation counting. Both the glucose incubated and non-glucose incubated products preferably are dissolved in water to a protein or polymer concentration approximating normal serum (73.5 g/L) levels. The fructosamine assay is run using calibrators consisting of glucose-incubated and non-glucose-incubated product and/or known mixtures of both products. A relationship between the concentration of glycogroups in the standards, for instance, as determined by standard isotopic measurement, to absorbance response of the fructosamine assay is run using calibrators consisting of glucose-incubated and non-glucose-incubated product and/or known mixtures of both products. A relationship between the concentration of glycogroups in the standards to absorbance response of the fructosamine reaction is determined. This relationship is linear and is used to determine glycated protein concentrations in unknown samples. Non-glucose-incubated poly-L-lysine or related polyamino acids causes no color response in the fructosamine reaction and is used as a zero standard.

In the second aspect of this invention, where secondary standards are prepared, human serum is substituted for poly-L-lysine in the above protocol, with two exceptions:

1) The serum is first dialyzed versus isotonic saline to remove any, or substantially all, of the unbound native glucose present.

2) Instead of lyophilization, the amount of protein present is measured via a standard protein assay and the glucose-incubated and non-glucose-incubated sera are adjusted to identical concentrations, approximating normal serum protein concentration.

Various known portions of the two products are mixed and the fructosamine assay is run, for example, with the method of Baker's patents or Rosenthal's patents or any of the other well known methods. A relationship between the concentration of glycogroups in the primary standards and the absorbance response of the fructosamine reaction is determined. This relationship is nearly linear, and linear regression analysis is used to determine the amount of native glycation in the non-glucose incubated serum by determining the absolute value of the x-intercept as shown in FIG. 1.

The secondary standards are then assigned fructosamine values by simple addition of the calculated level of native glycation to the measured level of incubated glycation.

Fructosamine calibrators, i.e., secondary standards, are then run alongside standards derived from either or both of the above procedures and their values are determined. These calibrators can then be included in a kit to measure fructosamine without the defects associated with the prior art techniques.

The nature of this invention and its improved aspects and advantages can be seen by reference to the following representative and illustrative examples.

EXAMPLE 1

In order to minimize highly reactive contaminants, [$^{14}$C]glucose preparations (Amersham) were treated by the method of Elbe, J. Biol. Chem. 258 9406 (1983). Purified [$^{14}$C]glucose was mixed with unlabeled glucose (10.7 mmol/L; 1.76 mCi/mole final concentration) and incubated with poly-L-lysine (Sigma product P-2636, average molecular weight=62,500, 73.5 g/L final concentration) in 46 mmol/L Trishydroxyaminoethane (Tris) buffer pH 8.0.

As a control, poly-L-lysine was incubated as above without glucose added. All reaction solutions were sterile-filtered prior to incubation. The incubations were performed at 60° C. for 46 hours. The products were then dialyzed versus deionized water (2 changes) over a period of five days. The dialysis solution was saved for glucose analysis. After removal from dialysis, the products were lyophilized. Liquid scintillation counting of the glucose-incubated product showed 285 DPM per 2.0 mg of product or 6.57 μg glucose/mg poly-L-lysine. Both products were dissolved in water to a concentration of 73.5 g/L. (The glucose incubated poly-L-lysine standard then contained 2.68 mmol/L glycogroups.) The products were analyzed for fructosamine content using calibrators assigned values based on DMF secondary standards, viz. GLYCO-Probe GSP, Isolab Inc. The non-glucose-incubated and glucose-incubated products showed 0.01 and 5.34 mmol/L fructosamine, respectively. Note that DMF calibration overestimated by a factor of about two, the actual fructosamine content of the sample. Also note that non-glucose-incubated poly-L-lysine produced only a minimal absorbance response (Absorbance responses: water blank 0.0004, non-glucose-incubated 0.0033, glucose incubated 0.4147, response slope=0.155 absorbance units/mmol glycogroups/liter) in the fructosamine assay.

The dialysis solution was also assayed for glucose content using both an enzymatic procedure (Sigma Glucose Reagent, Product #315-100) and using liquid scintillation counting. The glucose consumed during incubation was assumed to have reacted with the poly-L-lysine. Results of the two above methods showed 6.84 and 6.13 μg glucose/mg poly-L-lysine, respectively for the enzymatic procedure, versus the scintillation counting.

EXAMPLE 2

Human serum was extensively dialyzed versus isotonic saline at 4° C. to remove any glucose present. [$^{14}$C]Glucose, purified as in Example 1, was mixed with unlabeled glucose (58 mmol/L; 1.98 mCi/mol final concentration) and added to the serum along with 5.57 g/L of Tris buffer. The serum pH was then adjusted to pH 8.0 with 4N aqueous HCl. As a control, serum was also treated as above, except no glucose was added. Incubations were performed for 64.3 hours at 37° C. After incubation, the sera were dialyzed versus isotonic saline at 4° C. (3 days, 2 changes per day) and adjusted to pH 7.3 with 4N aqueous HCl. The sera were concentrated (using Amicon Centriflo cones, product #CF 25) to a nearly identical protein concentration (measured using Pierce BCA Protein Reagent, product #23225) of 71.5 ±0.5 g/L. Liquid scintillation counting of the glucose-incubated serum showed 1445 DPM/100 μL serum or 3.29 mmol/L glycogroups. The sera were analyzed for fructosamine content as in Example 1. The non-glucose-incubated serum (NG) had a fructosamine value of 2.02 mmol/L, the glucose (G) incubated serum had a value of 15.5 mmol/L. Volumes of the two sera were mixed as in Table 1. The various mixtures were assayed for fructosamine and glucose content (using a liquid scintillation counter) with results shown in Table 1.

TABLE 1

| A Mixture | B μL NG | C μL G | D DPM/50 μL -Bkg | E added mM glycogroups per liter | F Fructosamine absorbance response | G mM glycogroups per liter |
|---|---|---|---|---|---|---|
| 1 | 1000 | 0 | 0 | 0 | 0.0849 | 0.528 |
| 2 | 930 | 70 | 56 | 0.255 | 0.1254 | 0.783 |
| 3 | 850 | 150 | 113 | 0.512 | 0.1714 | 1.04 |
| 4 | 780 | 220 | 178 | 0.808 | 0.2178 | 1.33 |
| 5 | 700 | 300 | 239 | 1.091 | 0.2603 | 1.62 |

Column A: is the mixture number
Column B: indicates the uL of the non-glucose-incubated serum (NG) used in the mixture
Column C: indicates the uL of the glucose-incubated serum used in the mixture
Column D: the (DPM/50 uL)-BKG is the designation of disintegrations per minute per 50 uL minus the background reading for the mixture
Column E: indicates the calculated mM glycogroups per liter added
Column F: indicates the fructosamine absorbance responses obtained on the mixtures
Column G: indicates the values by the addition of the values from Column E with the value for mixture 1 in the column G Column E was calculated from the data in column D assuming $4.34 \times 10^9$ DPM/mole of glucose. Linear regression analysis was performed on the data in columns E (x-axis) and F (y-axis) and the results were plotted in FIG. 1. The first entry in column G is the absolute value of the X intercept (see FIG. 1) which is the amount of native glycosylation on this serum sample. The remaining values i.e. mixtures 2 to 5, in column G are calculated by addition of the values in column E. Note that the response slope in Example 1 for poly-L-lysine (0.155) and the response slope for serum (0.162) are nearly identical. This confirms that poly-L-lysine based standards are appropriate for calibrating the fructosamine assay.

EXAMPLE 3

[$^{14}$C]Glucose, purified as in Example 1, was mixed with unlabeled glucose (325 mmol/L; 0.323 mCi/mole final concentration) and incubated with each polyamino acid in Table 2 (58.8 g/L final concentration) in 46 mmol/L Tris buffer pH 8.0. Egg Albumin at the same final concentration was incubated also.

As a control, each polyamino acid in Table 2 was incubated as above without glucose added. All reaction solutions were sterile filtered prior to incubation. The incubations were performed at 37° C. for 47 hours. The products were dialyzed versus running deionized water for a period of three days. After removal from dialysis, the products were lyophilized. The products were dissolved in isotonic saline to a concentration of 10.5 g/L (except for egg albumin and poly-L-aspartic acid which were 73.5 g/L). The products were analyzed for [$^{14}$C]glucose content and fructosamine content as in Example 1. Results are shown in Table 2.

Note that the non-glucose-incubated polyamino acids produced no absorbance response in the fructosamine assay. Also note that, except for poly-DL-lysine and poly-L-lysine-glutamic acid, the absorbance response slopes are very similar.

TABLE 2

| Polyamino Acid | A | B | C | D | E | F |
| --- | --- | --- | --- | --- | --- | --- |
| L-lysine | 2.18 | −0.09 | 3.41 | −.0004 | .2308 | 0.106 |
| D-lysine | 2.42 | −0.10 | 4.60 | −.0010 | .3092 | 0.128 |
| DL-lysine | 3.20 | −0.10 | 9.15 | −.0007 | .6091 | 0.191 |
| L-lysine-alanine 2:1 | 2.79 | −0.09 | 4.01 | −.0001 | .2701 | 0.097 |
| L-lysine-serine 3:1 | 2.57 | −0.10 | 4.03 | −.0006 | .2717 | 0.106 |
| L-lysine-glutamic acid 4:1 | 3.01 | −0.09 | 5.17 | −.0003 | .3469 | 0.115 |
| L-aspartic acid | 0.73 | 0.02 | 0.05 | .0020 | .0045 | 0.003 |
| egg albumin | 2.78 | 0.62 | 3.98 | .0470 | .2968 | 0.090 |

Column A: mmol/L glycogroups for glucose incubated
Column B: mmol/L fructosamine (DMF equivalents) non-glucose incubated
Column C: mmol/L fructosamine (DMF equivalents) glucose incubated
Column D: absorbance response non-glucose incubated
Column E: absorbance response glucose incubated
Column F: response slope in absorbance units/mmol glycogroups/liter

EXAMPLE 4

Three serum pools, viz. secondary standards, with fructosamine contents of about 2, 3, and 4 mM DMF equivalents were aliquoted and lyophilized to be used as calibrators for the fructosamine assay. After reconstitution, these calibrators were run along with the poly-L-lysine standard (2.68 mM glycogroups) from Example 1 and also two serum samples (unknowns). Results are shown in Table 3.

This demonstrates that calibrators for the fructosamine assay can be assigned values in mM/L glycogroups from Poly-Lysine standards. The calibrators can then be used in separate runs (with or without using a standard) to determine patient serum (or plasma) fructosamine values.

TABLE 3

| Sample | Absorbance | mM/L glycogroups |
| --- | --- | --- |
| H$_2$O | .0002 | −0.01 |
| CALIB. 1 | .1391 | 0.98 |
| CALIB. 2 | .2174 | 1.54 |
| CALIB. 3 | .2745 | 1.95 |
| SERUM 1 | .1319 | 0.93 |
| SERUM 2 | .2507 | 1.78 |
| Poly-LYS non-glucose | .0010 | 0.00* |
| Poly-LYS glucose incubated | .3772 | 2.68* |

*assigned values, other values in this column are calculated.

EXAMPLE 5

Triazine dyes were reacted with glycated and nonglycated poly-L-lysine-glutamic acid 4:1 and poly-L-aspartic acid from example 3. The dyes used were reactive yellow 2 (Sigma #R-8003) and reactive red 4 (Sigma #R-7878). The dyes were first dissolved in 0.12M carbonate buffer pH 9.4 and mixed (1:1, v:v) with polyamino (1:1, v:v) acid solutions from example 3. The solutions were incubated for four days at 37° C. and then dialyzed versus running deionized water. The resulting products were lyophilized, redissolved in isotonic saline and filtered through glass fiber paper to remove insolubles. The dyed polymers were run on the Glyc-Affin Column Test Kit which is an affinity chromatographic method for determining the % glycated hemoglobin or protein in a sample. Results were recorded in table 4.

This demonstrates that glycated polyamino acids bind to the column to a greater extent than do their nonglycated counterparts. There is some nonspecific binding which occurs. This is probably due to ionic interactions of the affinity resin with the dyed polyamino acids. These dyed glycated polyamino acids could be used to determine column binding efficiency or as controls in the determination of glycated hemoglobin or glycated protein.

Thus, the glycated polyamino acids can be used alone, with a dye, or as a blend with a nonglycated polyamino acid, usually in the ratio to yield about 5–90% and preferably about 5–25% glycation. Any of the dyes that react, under the chosen conditions, with the glycated or non-glycated polyamino acids to produce a colored product can be used. The dyed glycated polyamino acids can be used in ion exchange column assays or related so-called affinity column assays. The triazine dyes are particularly preferred.

TABLE 4

| polyamino acid | glucose incubated | dye | wavelength | % glycated |
| --- | --- | --- | --- | --- |
| L-aspartic | N | red | 540 | 6.4% |
| L-aspartic | Y | red | 540 | 14.3 |
| L-lysine-glutamic | N | red | 540 | 12.4 |
| L-lysine-glutamic | Y | red | 540 | 16.9 |
| L-lysine-glutamic | N | yellow | 415 | 12.5 |
| L-lysine-glutamic | Y | yellow | 415 | 27.8 |

What is claimed is:

1. A primary standard to measure glycated protein comprising a solution of a water soluble synthetic polymer of at least one amino acid glycated by reaction with glucose to yield a glycated polymer having a known amount of reacted glucose and having any unreacted glucose removed therefrom and wherein said glycated polymer is dyed.

2. The primary standard of claim 1 wherein said water soluble synthetic polymer has a molecular weight in the range of from about 10,000 to 150,000.

3. The primary standard of claim 1 wherein said water soluble synthetic polymer is polylysine.

4. The primary standard of claim 1 wherein said water soluble synthetic polymer is a co-polymer of lysine and one or more other amino acids.

5. The primary standard of claim 4 wherein said other amino acids are selected from the group consisting of glycine, alanine, glutamic acid and tyrosine.

6. The primary standard of claim 1 wherein the known reacted glucose content is greater than 0 to 15 millimoles per liter of aqueous standard solution.

7. A method of preparing secondary glycated protein assay standard solutions comprising reaction glucose with a native protein solution so as to yield a glycated native protein solution, removing any unbound glucose from said glycated native protein solution, mixing a native protein solution with said glycated native protein solution to yield blended secondary standard protein solutions, and quantitating the amount of glycation in solutions by comparison of their glycated protein levels determined by a glycated protein assay with the glycated protein levels of a primary standard, said primary standard comprising a solution of a water soluble synthetic polymer of at least one amino acid glycated by reaction with glucose to yield a glycated polymer having a known amount of reactive glucose and having any unreacted glucose removed therefrom.

* * * * *

UNITED STATES PATENT AND TRADEMARK OFFICE
CERTIFICATE OF CORRECTION

PATENT NO. : 5,132,230
DATED : July 21, 1992
INVENTOR(S) : Murray A. Rosenthal, et al.

It is certified that error appears in the above-indentified patent and that said Letters Patent is hereby corrected as shown below:

Column 8, line 54, delete the word "reaction" and insert --reacting--.
Column 8, line 60, after "in" insert --said secondary standard protein--.

Signed and Sealed this

Nineteenth Day of October, 1993

Attest:

BRUCE LEHMAN

*Attesting Officer*    *Commissioner of Patents and Trademarks*